(12) United States Patent
Gandhi et al.

(10) Patent No.: US 7,138,032 B2
(45) Date of Patent: Nov. 21, 2006

(54) METHODS OF FABRICATING POLYMERIC STRUCTURES INCORPORATING MICROSCALE FLUIDIC ELEMENTS

(75) Inventors: Khushroo Gandhi, Sunnyvale, CA (US); Robert S. Dubrow, San Carlos, CA (US); Luc J. Bousse, Los Altos, CA (US)

(73) Assignee: Caliper Life Sciences, Inc., Mountain View, CA (US)

(*) Notice: Subject to any disclaimer, the term of this patent is extended or adjusted under 35 U.S.C. 154(b) by 220 days.

(21) Appl. No.: 10/359,959

(22) Filed: Feb. 6, 2003

(65) Prior Publication Data

US 2003/0150555 A1    Aug. 14, 2003

Related U.S. Application Data

(62) Division of application No. 09/590,661, filed on Jun. 7, 2000, now Pat. No. 6,555,067, which is a division of application No. 09/073,710, filed on May 6, 1998, now Pat. No. 6,123,798.

(51) Int. Cl.
*B32B 37/04* (2006.01)

(52) U.S. Cl. ..................... 156/292; 156/309.6

(58) Field of Classification Search ........ 156/290–292, 156/308.2, 308.4, 309.6, 309.9; 137/833–834; 204/450–451, 600–601; 428/167; 422/99–104, 422/130–131
See application file for complete search history.

(56) References Cited

U.S. PATENT DOCUMENTS

| | | | |
|---|---|---|---|
| 4,390,403 A | 6/1983 | Batchelder | |
| 4,576,850 A | 3/1986 | Martens | |
| 4,908,112 A | 3/1990 | Pace | |
| 5,126,022 A | 6/1992 | Soane et al. | |
| 5,250,263 A | 10/1993 | Manz | |
| 5,296,114 A | 3/1994 | Manz | |
| 5,376,252 A | 12/1994 | Ekstrom et al. | |
| 5,480,614 A | 1/1996 | Kamahori | |
| 5,498,392 A | 3/1996 | Wilding et al. | |
| 5,500,071 A | 3/1996 | Kaltenbach | |
| 5,571,410 A | 11/1996 | Swedberg et al. | |
| 5,585,069 A | 12/1996 | Zanzucchi et al. | |
| 5,593,838 A | 1/1997 | Zanzucchi et al. | |
| 5,599,432 A | 2/1997 | Manz et al. | |
| 5,603,351 A | 2/1997 | Cherukuri et al. | |
| 5,635,358 A | 6/1997 | Wilding et al. | |
| 5,637,469 A | 6/1997 | Wilding et al. | |
| 5,699,157 A | 12/1997 | Parce | |
| 5,750,015 A | 5/1998 | Soane et al. | |
| 5,779,868 A | 7/1998 | Parce et al. | |

(Continued)

FOREIGN PATENT DOCUMENTS

WO    WO-9429400    12/1994

(Continued)

OTHER PUBLICATIONS

Cohen, C.B. et al., "A microchip-based enzyme assay for protein kinase A," *Anal. Chem.* (1999) 273:89-97.

(Continued)

*Primary Examiner*—Jessica Rossi
(74) *Attorney, Agent, or Firm*—Donald R. McKenna; Ann C. Petersen

(57) ABSTRACT

The present invention generally provides improved methods of fabricating polymeric microfluidic devices that incorporate microscale fluidic structures, whereby the fabrication process does not substantially distort or deform such structures. The methods of the invention generally provide enhanced bonding processes for mating and bonding substrate layers to define the microscale channel networks therebetween.

15 Claims, 5 Drawing Sheets

U.S. PATENT DOCUMENTS

| | | |
|---|---|---|
| 5,800,690 A | 9/1998 | Chow et al. |
| 5,842,787 A | 12/1998 | Kopf-Sill et al. |
| 5,852,495 A | 12/1998 | Parce |
| 5,858,188 A | 1/1999 | Soane et al. |
| 5,869,004 A | 2/1999 | Parce et al. |
| 5,876,675 A | 3/1999 | Kennedy |
| 5,880,071 A | 3/1999 | Parce et al. |
| 5,882,465 A | 3/1999 | McReynolds |
| 5,885,470 A | 3/1999 | Parce |
| 5,932,315 A | 8/1999 | Lum |
| 5,942,443 A | 8/1999 | Parce et al. |
| 5,948,227 A | 9/1999 | Dubrow |
| 5,955,028 A | 9/1999 | Chow |
| 5,957,579 A | 9/1999 | Kopf-Sill et al. |
| 5,958,203 A | 9/1999 | Parce et al. |
| 5,958,694 A | 9/1999 | Nikiforov |
| 5,959,291 A | 9/1999 | Jensen |
| 5,964,995 A | 10/1999 | Nikiforov et al. |
| 5,965,001 A | 10/1999 | Chow et al. |
| 5,965,410 A | 10/1999 | Chow et al. |
| 5,972,187 A | 10/1999 | Parce et al. |
| 5,976,336 A | 11/1999 | Dubrow et al. |
| 5,989,402 A | 11/1999 | Chow et al. |
| 6,001,231 A | 12/1999 | Kopf-Sill |
| 6,004,515 A | 12/1999 | Parce et al. |
| 6,011,252 A | 1/2000 | Jensen |
| 6,012,902 A | 1/2000 | Parce |
| 6,042,709 A | 3/2000 | Parce et al. |
| 6,042,710 A | 3/2000 | Dubrow |
| 6,046,056 A | 4/2000 | Parce et al. |
| 6,048,498 A | 4/2000 | Kennedy |
| 6,054,034 A * | 4/2000 | Soane et al. ................ 204/601 |
| 6,068,752 A | 5/2000 | Dubrow et al. |
| 6,168,948 B1 * | 1/2001 | Anderson et al. ........ 435/287.2 |
| 6,171,850 B1 | 1/2001 | Nagle et al. |
| 6,176,962 B1 | 1/2001 | Soane et al. |
| 6,337,212 B1 | 1/2002 | Nagle et al. |

FOREIGN PATENT DOCUMENTS

| | | |
|---|---|---|
| WO | WO-9604547 | 2/1996 |
| WO | WO-9702357 | 1/1997 |

OTHER PUBLICATIONS

Dasgupta, P.K. et al., "Electroosmosis: A Reliable fluid Propulsion System for Flow Injection Analysis," Anal. Chem. 66:1792-1798 (1994).

Jacobson, S.C. et al., "Fused Quartz Substrates for Microchip Electrophoresis," Anal. Chem. 67:2059-2063 (1995).

Knovel.com Polyehtylene, Polydimethylsiloxane.

Manz, A. et al., "Electroosmotic pumping and electrophoretic separations for miniaturized chemical analysis systems," J. Micromech. Microeng. 4:257-265 (1994).

Manz, A. et al., "Parallel Capillaries for High Throughput in Electrophoretic and Electroosmotic Drug Discovery Systems," Transducers 97 Chicago, IL Jun. 16-19, 1997 2:915-918.

McCormick, R.M. et al., "Microchannel electrophoretic Separations of DNA in Injection-Molded Plastic substrates," Anal. Chem. 69:2626-2630 (1997).

Milby, R.V., Plastics Technology, McGraw-Hill Book Company, New York, pp. 305-306, 529-530 (1973).

Modern Plastics Encyclopedia, Oct. 1983, vol. 60, No. 10A.

Ramsey, J.M. et al., "Microfabricated chemical measurement systems," Nature Med. 1:1093-1096 (1995).

Seiler, K. et al., "Planar Glass Chips for Capillary Electrophoresis: Repetitive Sample Injection, Quantitation, and Separation Efficiency," Anal. Chem. 65:1481-1488 (1993).

Seiler, K. et al., "Electroosmotic Pumping and Valveless Control of Fluid Flow within a Manifold of Capillaries on a Glass Chip," Anal. Chem. 66:3485-3491 (1994).

Sundberg, S., "High-throughput and ultra-high-throughput screening: solution- and cell-based approaches," *Current Opin. In Biotech.* (2000) 11:47-53.

Taylor, J.W. et al., "Applied approach to film formation", http://www.coatings.de/articles/taylor.pdf.

Woolley, A.T. et al., "High-Speed DNA Genotyping Using Microfabricated Capillary Array Electrophoresis Chips," Anal. Chem. 69:2181-2186 (1997).

* cited by examiner

US 7,138,032 B2

METHODS OF FABRICATING POLYMERIC STRUCTURES INCORPORATING MICROSCALE FLUIDIC ELEMENTS

CROSS-REFERENCE TO RELATED APPLICATION

This application is a division of U.S. patent application Ser. No. 09/590,661, filed Jun. 7, 2000, now U.S. Pat. No. 6,555,067 B1, which is a division of U.S. patent application Ser. No. 09/073,710, filed May 6, 1998, now U.S. Pat. No. 6,123,798.

BACKGROUND OF THE INVENTION

As with the electronics and computer industries, trends in chemical and biochemical analysis are moving toward faster, smaller and less expensive systems and methods for performing all types of chemical and biochemical analyses.

The call for smaller systems and faster methods has been answered, in part, through the development of microfluidic technologies, which perform chemical and biochemical analyses and syntheses in extremely small-scale integrated fluid networks. For example, published International Patent Application No. WO 98/00231 describes microfluidic devices, systems and methods for performing a large number of screening assays within a single microfluidic device that is on the order of several square centimeters. Such developments have been made possible by the development of material transport systems that are capable of transporting and accurately dispensing extremely small volumes of fluid or other materials. See Published International Application No. 96/04547 to Ramsey.

By accurately controlling material transport among a number of integrated channels and chambers, one is able to perform a large number of different analytical and/or synthetic operations within a single integrated device. Further, because these devices are of such small scale, the amount of time for reactants to transport and/or mix, is very small. This results in a substantial increase in the throughput level of these microfluidic systems over the more conventional bench-top systems.

By reducing the size of these microfluidic systems, one not only gains advantages of speed, but also of cost. In particular, these small integrated devices are typically fabricated using readily available microfabrication technologies available from the electronics industries which are capable of producing large numbers of microfluidic devices from less raw materials. Despite these cost savings, it would nonetheless be desirable to further reduce the costs required to manufacture such microfluidic systems.

A number of reporters have described the manufacture of microfluidic devices using polymeric substrates. See, e.g., Published International Patent Application No. WO 98/00231 and U.S. Pat. No. 5,500,071. In theory, microfabrication using polymer substrates is less expensive due to the less expensive raw materials, and the 'mass production' technologies available to polymer fabrication and the like.

However, despite these cost advantages, a number of problems exist with respect to the fabrication of microfluidic devices from polymeric materials. For example, because polymeric materials are generally flexible, a trait that is accentuated under certain fabrication methods, e.g., thermal bonding, solvent bonding and the like, it is difficult to accurately manufacture microscale structural elements in such polymeric materials. In particular, the microscale structures are easily deformed under manufacturing conditions, either due to applied pressures or relaxation of the polymer matrix based upon its intrinsic structural properties.

Accordingly, it would generally be desirable to have a method of fabricating microscale devices where the structural aspects of the device are not substantially perturbed during the fabrication process. The present invention meets these and other needs.

SUMMARY OF THE INVENTION

It is a general object of the present invention to provide methods of fabricating polymeric microfluidic devices, and the devices fabricated using these methods. In a first aspect, the present invention provides for methods of fabricating a microfluidic device comprising a first substrate having a first planar surface, and a second substrate layer having a first planar surface, wherein the first planar surface of the first substrate comprises a plurality of microscale grooves disposed therein. The first planar surface of the second substrate is heated approximately to the transition temperature of the first surface of the second substrate without heating the first surface of the first substrate approximately to the transition temperature of the first surface of the first substrate. The first surface of the first substrate is then bonded to the first surface of the second substrate.

This invention also provides methods of fabricating a microfluidic device comprising a first substrate having a first planar surface, and a second substrate layer having a first planar surface wherein the first planar surface of the first substrate comprises a plurality of microscale grooves disposed therein, and the first planar surface of the second substrate has a lower transition temperature than the first surface of the first substrate. The first planar surface of the second substrate is heated approximately to its transition temperature. The first surface of the first substrate is then bonded to the first surface of the second substrate.

This invention also provides methods of fabricating microfluidic devices comprising a first substrate having a first planar surface, and a second substrate layer having a first planar surface, wherein the first planar surface of the second substrate has a lower transition temperature than the first surface of the first substrate. The first surface of the second substrate is heated approximately to the transition temperature. The first surface of the first substrate is bonded to the first surface of the second substrate.

This invention also provides methods of fabricating a microfluidic device comprising a first substrate having at least a first surface and a second substrate having at least a first surface, wherein at least one of the first surface of the first substrate or the first surface of the second substrate comprises a textured surface, and mating and bonding the first surface of the first substrate to the first surface of the second substrate.

This invention also provides methods of fabricating a microfluidic device comprising a first substrate having a first planar surface, and a second substrate layer having a first planar surface, wherein the first planar surface of the second substrate has a lower transition temperature than the first surface of the first substrate. The first surface of the first substrate is thermally bonded to the first surface of the second substrate, whereby the first surface of the second substrate does not substantially project into the plurality of channels.

This invention also provides a microfluidic device comprising a first polymeric substrate having at least a first planar surface, the first planar surface comprising a plurality of channels disposed therein. The device also includes a second polymeric substrate layer having at least a first planar surface, the first planar surface of the second substrate is bonded to the first planar surface of the first substrate, and wherein the first surface of the second substrate has a lower transition temperature than the first surface of the first substrate.

This invention also provides a microfluidic device comprising a first polymeric substrate comprising a first planar surface having a plurality of microscale channels disposed therein. The device also contains a second polymeric substrate comprising a first planar surface, the first planar surface of the second substrate being non-solvent bonded to the first planar surface of the first substrate, wherein the first surface of the second substrate does not substantially project into the plurality of channels.

BRIEF DESCRIPTION OF THE FIGURES

FIG. 2 illustrates examples of channel deformation in some methods of fabricating layered polymeric microstructures.

FIG. 3 illustrates an example of surface texturing utilized to fabricate layered polymeric microstructures.

DETAILED DESCRIPTION OF THE INVENTION

I. General

As noted above, the present invention generally provides improved methods of fabricating polymeric microfluidic devices. Generally, these improved methods allow for the rapid fabrication of polymeric devices that incorporate microscale fluidic structures, whereby the fabrication process does not substantially distort or deform such structures.

As used herein, the term "microscale" or "microfabricated" generally refers to structural elements or features of a device which have at least one fabricated dimension in the range of from about 0.1 μm to about 500 μm. Thus, a device referred to as being microfabricated or microscale will include at least one structural element or feature having such a dimension. When used to describe a fluidic element, such as a passage, chamber or conduit, the terms "microscale," "microfabricated" or "microfluidic" generally refer to one or more fluid passages, chambers or conduits which have at least one internal cross-sectional dimension, e.g., depth, width, length, diameter, etc., that is less than 500 μm, and typically between about 0.1 μm and about 500 μm. In the devices of the present invention, the microscale channels or chambers preferably have at least one cross-sectional dimension between about 0.1 μm and 200 μm, more preferably between about 0.1 μm and 100 μm, and often between about 0.1 μm and 20 μm. Accordingly, the microfluidic devices or systems prepared in accordance with the present invention typically include at least one microscale channel, usually at least two intersecting microscale channels, and often, three or more intersecting channels disposed within a single body structure. Channel intersections may exist in a number of formats, including cross intersections, "T" intersections, or any number of other structures whereby two channels are in fluid communication.

In particularly preferred aspects, the microfluidic devices described herein, are used in conjunction with controlled electrokinetic material transport systems, as described in Published International Application No. 96/04547 to Ramsey, which is incorporated herein by reference for all purposes. Specifically, such material transport systems are used to transport fluid and/or other materials through the interconnected channels of the devices in a controlled fashion.

Figure 1:
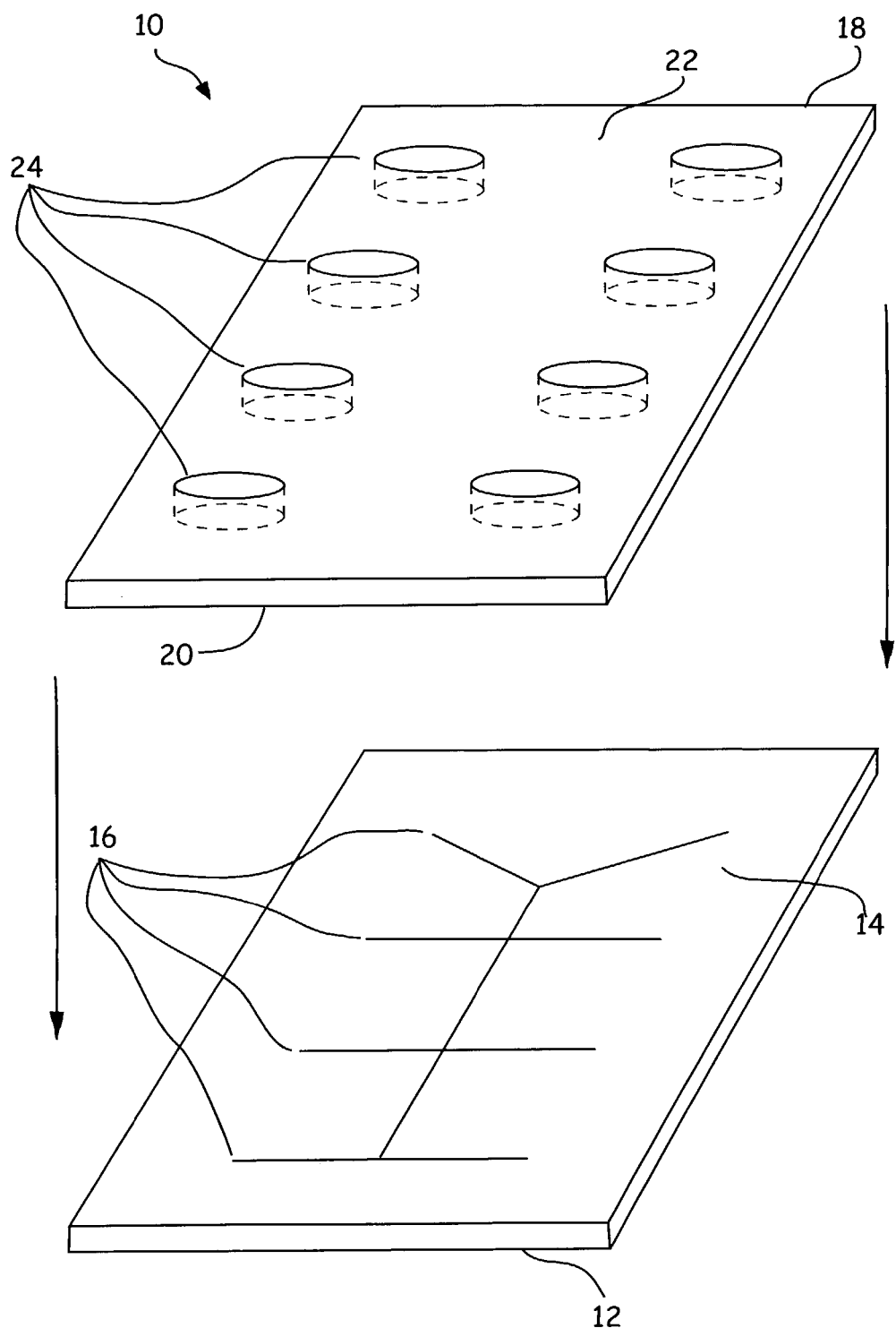
FIG. 1 is a schematic illustration of a microfluidic device incorporating a layered structure.

The microfluidic devices in accordance with the present invention include a body structure that has disposed therein, an integrated network of microscale channels or conduits. The different elements of the body structure may be fabricated from a number of different separate parts to define the various channels and/or chambers of the device. In particularly preferred aspects, the body structure of the device is fabricated as a layered structure. An example of a device incorporating this layered structure is illustrated in FIG. 1. In particular, the device 10, includes a bottom portion 12 which comprises a solid substrate that is substantially planar in structure, and which has at least one substantially flat upper surface 14.

The channels and/or chambers of the microfluidic device are typically fabricated into the upper surface of the bottom substrate or portion 12, as microscale grooves or indentations 16, using the microfabrication techniques described herein. The top portion or substrate 18 also comprises a first planar surface 20, and a second surface 22 opposite the first planar surface 20. In the microfluidic device shown in FIG. 1, the top portion of the device optionally includes a plurality of apertures, holes or ports 24 disposed therethrough, e.g., from the first planar surface 20 to the second surface 22 opposite the first planar surface.

The first planar surface 20 of the top substrate 18 is then mated, e.g., placed into contact with, and bonded to the planar surface 14 of the bottom substrate 12, covering and sealing the grooves and/or indentations 16 in the surface of the bottom substrate, to form the channels and/or chambers (i.e., the interior portion) of the device at the interface of these two components. In those embodiments utilizing incorporated reservoirs or ports, the holes 24 in the top portion of the device are oriented such that they are in communication with at least one of the channels and/or chambers formed in the interior portion of the device from the grooves or indentations in the bottom substrate. In the completed device, these holes function as the reservoirs for facilitating fluid or material introduction into the channels or chambers of the interior portion of the device, as well as providing ports at which electrodes may be placed into contact with fluids within the device, allowing application of electric fields along the channels of the device to control and direct fluid transport within the device.

As noted above, at least one, and preferably both or all of the substrate layers, e.g., as described with reference to FIG.

1, comprise a polymeric material or substrate. In accordance with the present invention, the polymeric substrate materials used to fabricate the microfluidic devices described herein are typically selected from a wide variety of different polymeric materials. Examples of particularly useful polymer materials include, e.g., polymethylmethacrylate, polycarbonate, polytetrafluoroethylene, polyvinylchloride, polydimethylsiloxane, polysulfone, polystyrene, polymethylpentene, polypropylene, polyethylene, polyvinylidine fluoride, and acrylonitrile-butadiene-styrene copolymer.

Because microscale fluidic structures are of such small dimensions, e.g., channel depths typically falling in the range of from about 1 to 50 µm, even slight deformation of a channel's structure can have seriously adverse effects on the function of the device incorporating that channel, including partial or total channel occlusion, formation of sharp corners in the channels along which irregular capillary flow occurs, structural irregularities causing disruptive flow patterns during operation, and the like.

Unfortunately, channel distortion of the type referred to above, is exactly the type of problems faced in fabricating polymeric microfluidic devices. In particular, in preferred aspects, the microfluidic devices of the present invention are fabricated as an aggregation of different substrate layers that are typically planar in structure. One of the layers typically includes a series of grooves and/or depressions fabricated into its surface, which grooves or depressions define the channels and chambers of the ultimate microfluidic device. A second layer is overlaid and bonded to the first layer to seal the grooves and depressions forming the channels and chambers. Optionally, the channels and/or chambers are defined in an intermediate layer, which defines the sides of the channels and/or chambers. The intermediate layer is then sandwiched and bonded between the top and bottom layers, which form the top and bottom surfaces, respectively, of the channels and/or chambers. The substrate layers are then bonded together using known bonding techniques. For polymeric substrates, such techniques include, e.g., thermal bonding, ultrasonic bonding or welding, adhesive bonding, or solvent bonding.

In thermal bonding of solid polymeric substrates, one or more of the substrates to be bonded is heated to the transition temperature of the substrate surface. As used herein, the "transition temperature" refers to the temperature at which the polymer substrate material, which normally has a glass-like character, undergoes the transformation from a rigid material to a soft rubber, e.g., the melting point. In particular, as a polymer is heated to a temperature at or just below the transition temperature, the polymer starts to soften. In the case of non-crystalline polymeric materials, the transition temperature is typically referred to as the "glass transition temperature," typically denoted by $T_g$. At the glass transition temperature, the glass-like polymer begins to take on the more rubbery character.

For non-polymeric substrates, e.g., glass, quartz, silicon and the like, the substrate is typically sufficiently hard that even under extremely high bonding temperatures, e.g., in excess of 500° C., there is substantially no deformation of the microscale channels between the substrates being bonded. For polymeric substrates, however, substantial deformation can occur during thermal bonding at substantially lower temperatures.

For example, when polymeric substrates are heated to their transition temperature and bonded together, microscale structural elements have a tendency to flatten under the elevated temperatures and pressures. Similarly, otherwise flat substrate layers have a tendency to be extruded into cavities, depressions or grooves on the opposite substrate surface, e.g., channels and/or chambers, as a result of their softer character and the effects of the applied pressure. This extrusion of an upper substrate layer into a channel or chamber creates a number of problems. For example, such extrusion results in unknown or variable volumes for the channels and chambers, and also results in substantial occlusion of channels. Further, and as referenced above, this channel extrusion can result in the generation of fluid shooters, where fluids in the corners of channels move much faster than the remainder of the fluid. These shooters have a tendency to travel far ahead of the bulk fluid front in capillary filling of channels, and join together to trap air bubbles within the channels. The presence of such air bubbles, particularly in extremely small-scale channels can be fatal to the proper operation of the device.

In the case of injection molded polymeric parts, additional problems are associated with the fabrication of polymeric devices. For example, in the injection molding process, polymeric material injected into a mold has a tendency to align the individual polymer molecule strands in the molded product in the direction of polymer injection. This alignment of polymer molecules results in an inherent or "frozen" stress in the hardened product as the polymer strands tend toward their natural random state. This frozen stress often results in a disproportionate shrinking of the molded part in the length dimension of the aligned polymers, as compared to the width, when the parts are heated to or near their transition temperatures, e.g., for thermal bonding. This shrinking then leads to deformation of microscale structures on the polymer part, and even warping of the part as a whole.

Figure 2A:
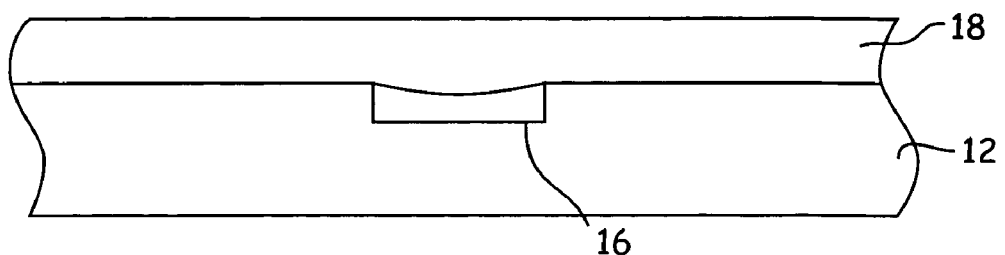
FIG. 2A illustrates the extrusion of a cover layer substrate into a channel structure fabricated into the surface of another substrate when the two substrates are thermally bonded together using conventional means.

FIG. 2 illustrates some examples of the types of channel deformation that occur during these types of thermal bonding processes for polymeric substrates. FIG. 2A illustrates the extrusion of an upper substrate layer into a channel structure fabricated on the lower substrate layer following thermal bonding of the substrates. Although illustrated as a drawing, the dimensions provided represent actual and substantial encroachment of the upper substrate into the channel. This was a result of heating the layers to above the transition temperature for the material used, and applying pressure to the two substrates to facilitate bonding. As shown, the upper layer encroaches upon the channel structure resulting in reduced performance of the device incorporating this channel, as described above.

Figure 2B:
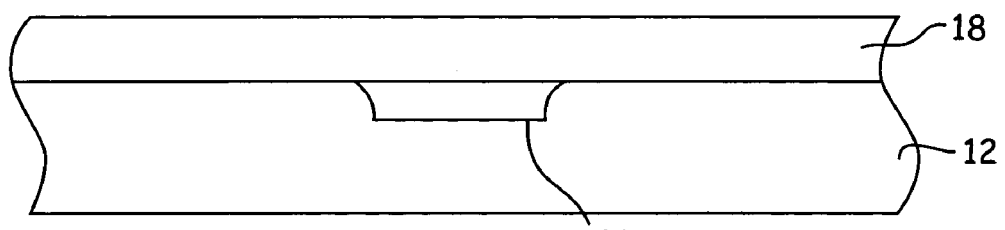
FIG. 2B illustrates the softening or dulling of channel corners in a thermally bonded polymeric microfluidic device, where the channel bearing structure is injection molded, or otherwise has residual stresses frozen into the structure.

FIG. 2B illustrates an example of thermally bonded polymeric substrates where the lower substrate, bearing the channel structure was injection molded, or otherwise had stresses frozen into it. Relaxation of the polymers in the substrate when the substrate was heated during thermal bonding resulted in a dulling of the channel edges.

One alternative to thermal bonding is ultrasonic welding or bonding. In these methods, a series of sharp protrusions or ridges ("energy directors") are fabricated on one of the parts to be bonded. Under elevated pressure and high frequency vibrations, these energy directors melt and bond with the corresponding surface on the other substrate. Again, however, use of such methods generally results in excessive channel distortion or irregularity, such that such the methods are not useful in fabrication of microscale fluidic devices. In particular, the edges of the bonded regions resulting from these ultrasonic methods tend to be relatively irregular in comparison with the edges of the channels. As such, the corners at which the two substrates meet will also be irregular, as a result of some material encroaching into the channel, and/or openings where the bonded edge does not reach the channel edge. These latter irregularities cause substantial difficulty in microfluidic systems as they can give rise to fluid "shooters" (edges of a channel at which capillary flow is faster than capillary flow in the rest of the channel) during fluid introduction and movement within the channel.

Another alternative to thermal bonding is the use of adhesives to bond polymeric parts together. The use of adhesives alleviates the problems of thermal deformation of channel structures. However, in order to be effective in the fabrication of microfluidic systems, adhesive must be carefully applied in order to ensure that the channels and chambers will be entirely sealed after bonding. Further, because microfluidic devices are generally used in sensitive analytical operations, it is generally desirable to avoid introducing any unwanted chemical components into the channels and/or chambers of the device. Thus, while one must ensure application of adequate adhesive to ensure sealing, one must avoid getting the adhesive into the extremely small scale channels and chambers. In addition to adverse chemical interactions, such contaminants can potentially produce structural barriers or occlusions which adversely affect fluid movement.

Another method of bonding polymeric substrates is through the use of solvent bonding processes. Typically, these processes involve the mating of two polymeric parts followed by application of a polymer softening solvent to the space between the parts, e.g., via capillary action. The softening and re-hardening of the polymer interface results in a bonded part. Solvent bonding methods are well known in the art and are described in, e.g., Plastics Technology, Robert V. Milby (McGraw-Hill 1973), and Handbook of Plastics Joining: A Practical Guide (Plastics Design Library, 1996), both of which are incorporated herein by reference. The same contamination problems associated with adhesive bonding are also present in solvent bonding methods. Further, such solvent process typically cause at least some level of polymer softening which can lead to adverse structural effects, e.g., as described above. In addition, solvent bonding processes will often produce stress cracking when used in conjunction with injection molding processes.

II. Polymer Selection

In a first aspect, the methods of the present invention generally address the problems typically associated with the fabrication of microfluidic devices from polymeric substrates. In preferred aspects, the methods described herein are directed to thermal bonding methods of fabricating microfluidic devices. Accordingly, the methods of the invention are generally described with reference to the fabrication of microfluidic devices that incorporate a layered structure. Such devices typically include a top portion, a bottom portion, and an interior portion that is defined by the mating of the top portion to the bottom portion. Typically, a first substrate is provided which includes at least one planar surface. The microscale structural elements of the device are generally fabricated into the first surface of the first substrate. In the case of microscale fluidic channels and/or chambers, the structures typically are fabricated as microscale grooves or depressions in that surface.

In addition to the channel structures of the device fabricated into the first substrate surface, the second substrate also typically includes a plurality of apertures disposed through it. Each aperture is generally provided so as to be placed in fluid communication with at least one channel that is disposed within the interior portion of the device when the layers are bonded together. These apertures then function as the fluid reservoirs of the device, as well as points of access to the channel structures, e.g., for fluid introduction, electrical sensing and controlled electrokinetic material transport, and the like.

Fabrication of the grooves in the substrate surface is generally carried out using known polymer fabrication methods, e.g., injection molding, embossing, or the like. In particular, master molds or stamps are optionally created from solid substrates, such as glass, silicon, nickel electroforms, and the like, using well known microfabrication techniques. These techniques include photolithography followed by wet chemical etching, LIGA methods, laser ablation, thin film deposition technologies, chemical vapor deposition, and the like. These masters are then used to injection mold, cast or emboss the channel structures in the planar surface of the first substrate surface. In particularly preferred aspects, the channel or chamber structures are embossed in the planar surface of the first substrate.

By embossing the channel structures into the first substrate, one avoids the stress relaxation problems associated with injection molded substrates. In particular, because embossed substrates are not flowed or injected into a mold, there is substantially less alignment of the polymer strands from flowing of the polymer material. Accordingly, during thermal bonding, there is substantially less relaxation of the overall substrate when the substrates are mated, and therefore, substantially less channel deformation.

Typically, the grooves fabricated into the surface of the first substrate are fabricated as a series of intersecting grooves, to form the integrated intersecting channel structures of the devices of the invention. The grooves are formed into channels by mating a second substrate layer to the first, to cover and seal the grooves and/or depressions to form the channels and/or chambers of the device. In accordance with one aspect of the invention, the second substrate is thermally bonded to the surface of the first substrate over the channels. The surfaces of the two substrates are typically planar to permit adequate contact across the surface.

In order to avoid additional distortion of channel structures on the first substrate during the thermal bonding of the second substrate, the first and second substrates are typically selected to have differing transition temperatures. In particular, the substrate that bears the microscale structures is typically selected to have a higher transition temperature than the cover layer that is to be bonded to it. Selection of the channel bearing substrate to have a higher transition temperature, allows the cover layer to be heated to its transition temperature and mated with the channel bearing substrate, without distorting or deforming the channel structures on the channel bearing substrate. Of course, depending upon the desired goal, the channel bearing substrate may be selected to have a lower transition temperature, e.g., if substrate extrusion into the channels is the most critical, or only actual problem to be addressed. In particularly preferred aspects, both substrate layers are selected to minimize both channel distortion and channel occlusion problems, by selecting substrates that are sufficiently different in their transition temperatures to prevent channel distortion, but sufficiently close to prevent excessive extrusion of the upper substrate into the channel structures. Selection of a polymer having a higher transition temperature for the channel bearing substrate, permits the use of injection molded parts. Specifically, because these substrates do not need to be heated to their transition temperatures for thermal bonding, there is less chance of the substrate relaxing, and thus, resulting in deformation of the channels.

In preferred aspects, the transition temperature of the two substrates are at least about 5° C. apart, more preferably at least about 10° C. apart, more preferably, at least 20° C. apart, often at least 50° C., and in some cases, at least 100° C. apart. For example, where one substrate (that having the lower transition temperature) has a transition temperature of approximately 80° C., the other substrate will typically have a transition temperature of at least 85° C., preferably at least 90° C., more preferably at least 100° C., often at least 130°, and in some cases at least 180° C. Generally speaking, the transition temperature of the substrate having the higher transition temperature is typically at least 40° C., while the transition temperature of the substrate having the lower transition temperature is less than 150° C. Alternatively, the surface of one substrate is heated to its transition temperature while the surface of the other substrate is maintained at a lower temperature. As above, the first substrate is typically heated to a temperature at least 5° C., 10° C., 20° C., 50° C. or even at least 100° above the temperature at which the other substrate is maintained.

Thus, in accordance with the methods described herein, the planar surface of one of the substrates, typically the cover layer substrate, is heated approximately to the surface's transition temperature, without reaching the transition temperature of the surface of the other substrate, e.g., the channel bearing substrate. Typically, the entire polymeric part is fabricated from a single polymer, and thus the transition temperature of the surface is the same as the remainder of the substrate. However, it will be appreciated that multilayer polymeric materials are also envisioned in accordance with the present invention, including polymer substrates bearing a different polymer coating.

Following the heating of the substrates to the first transition temperature, the substrates are bonded together. In most but not all cases, this typically involves the application of slight pressure to the two substrates, pressing their bonding surfaces together, to ensure adequate and complete bonding of the parts. In those cases where a pressure is applied between the substrates, the amount of applied pressure is typically dependent upon the polymers and temperatures used. However, in general, the applied pressures are generally in the range of from about 0.1 kg/cm$^2$ to about 20 kg/cm$^2$.

In preferred aspects, the polymeric substrate materials used in accordance with this aspect of the invention comprise polymethylmethacrylate (PMMA), polycarbonate, polytetrafluoroethylene (TEFLON™), polyvinylchloride (PVC), polydimethylsiloxane (PDMS), polysulfone, polystyrene, polymethylpentene, polypropylene, polyethylene, polyvinylidine fluoride, ABS (acrylonitrile-butadiene-styrene copolymer), and the like. In many aspects, the present invention utilizes those polymers which are generally non-crystalline in structure, i.e., polymethylmethacrylate, polycarbonate, polyvinylchloride, polydimethylsiloxane, polysulfone, polystyrene, polymethylpentene, polyvinylidine fluoride, and acrylonitrile-butadiene-styrene copolymer In particularly preferred aspects, both substrates comprise polymethylmethacrylate grades. In order to provide a different transition temperature for the second substrate, or cover layer, this substrate typically comprises an injection moldable grade of PMMA. Examples of such polymeric materials include, e.g., Acrylite polymers, e.g., M-30, L-40, etc., available from CYRO Industries, for injection moldable grades of PMMA and Plexiglas V-825, available from Atohaas, North America, for the structure bearing substrate, which has a higher transition temperature. Typically, adjustment of the transition temperature is accomplished through the adjustment of the polymer composition, i.e., incorporating different amounts of other comonomers. For example, for PMMA, lower transition temperatures, e.g., for injection moldable grades of PMMA, are generally achieved by incorporating other acrylic comonomers, i.e., ethylacrylate, methylacrylate or butylacrylate monomers, during the synthesis of the polymer. Similarly, for polycarbonate polymers, transition temperatures are generally adjusted by incorporation of bisphenol analogs during synthesis, and adjusting their relative concentration. In the case of ABS polymers, transition temperatures may be adjusted by adjusting the relative level of the polymers in the combination, e.g., acrylonitrile, butadiene and styrene. Optionally, with the addition of other additives, i.e., tackifiers, waxes and the like, one can increase adhesive properties of substrate surfaces at or below the transition temperature of the bulk substrate material, thereby giving the surface of the substrate a lower effective transition temperature or "bonding temperature."

Transition temperatures are then adjusted by adjusting the relative percentages of these other monomers, i.e., increasing to reduce transition temperature. Typically, these additional monomers are present in the overall polymer at a concentration of at least about 0.1%, 1%, 2% and often at least about 5% or 10% or even greater, based upon the total monomer concentration used in the polymer synthesis, depending upon the desired transition temperature range.

Alternatively, or additionally, transition temperatures for polymers may be adjusted by adjusting the molecular weight of the polymers. In particular, longer and larger polymers typically have higher transition temperatures than smaller, shorter polymers. Thus, a substrate fabricated from a polymer having a lower average molecular weight, has a lower transition temperature than a polymer having a higher average molecular weight. In such cases, the polymer having the larger average molecular weight (and higher transition temperature) is at least about 5% larger than the average molecular weight of the other substrate (having the lower transition temperature), preferably, at least about 10% larger, more preferably at least about 20% larger, 50% and often at least 100%, and in many cases, at least about 200% larger than the polymer used to fabricate the other substrate having the lower transition temperature.

As noted above, the methods of the present invention result in the fabrication of microfluidic devices where the channel structures are not substantially distorted. In addition, these devices are characterized in that the cover layer substrate that is bonded to the channel bearing substrate does not substantially encroach upon, occlude or otherwise project into the channels of the device. The phrase "does not substantially project into the channel," as used herein, means that the cross-sectional area of the channel structure as it is defined by the structure bearing substrate (width of fabricated channel X depth of fabricated channel), is not substantially blocked by extrusion of the cover layer substrate into the channel. Such occlusion is shown in FIG. 2A. Typically, the cover layer occludes the cross-sectional area of the channels by less than 20% of the potential channel cross-section. In preferred aspects, the occlusion is less than 10% of the total cross-sectional area of the channel, and more preferably, less than 5% of the total cross-sectional area, and still more preferably, less than 2% occlusion of the total cross-sectional area. While solvent bonding methods are generally capable of producing devices where the cover layer does not substantially occlude the channels of the device, such solvent bonding methods have a number of other disadvantages, as described above. In the present invention, such non-occluded channels are fabricated in non-solvent bonding and/or non-adhesive bonding methods, e.g., bonding methods that do not utilize solvents or adhesives, i.e., thermal bonding, ultrasonic bonding, or the like.

III. Surface Textures

In an alternate aspect, the present invention provides methods of fabricating microfluidic devices from polymeric substrates by providing at least one of the substrates with a textured surface to assist bonding. In particular, as noted above, the use of excessive temperatures and/or excessive pressures during thermal bonding of polymeric substrates often results in deformation of the channel structures, and/or occlusion of the channels by the upper substrate layers being extruded into the channels. Like the above described aspects, the present embodiment of the invention improves thermal bonding and other methods of bonding polymeric substrates by reducing the temperatures and pressures to which a substrate is exposed during the bonding process. In accordance with this aspect of the invention, pressures and/or temperatures for bonding are minimized by reducing the effective surface area at which bonding occurs. In particular, the methods of the present invention provide one or both of the substrate layers having a textured bonding surface. By "textured bonding surface" is meant that the surface of the substrate that mates with and is bonded to the other substrate includes a structural texturing, such as a series of raised ridges, pillars, posts, or the like, that are disposed on the surface in question. Texturing of the bonding surfaces may take on a variety of forms. For example, the texturing optionally includes a series of parallel raised ridges/grooves fabricated into the bonding surface. Other textures are also useful in accordance with the present invention, including raised ridges fabricated in a grid or diamond pattern, raised pillars or posts fabricated in sufficiently close proximity that upon bonding, the spaces between them will be filled in and sealed.

In particularly preferred aspects, the surface texture is applied to the bonding surface of the substrate bearing the channel structures. Specifically, the microfabrication steps applied to the manufacture of the channel structures, i.e., embossing, injection molding, etc., can be exploited in the fabrication of the surface texturing. In addition, in preferred aspects, the surface texture is applied to the surface into which the channel structures are fabricated. As such, the texture is not present within the channel itself, e.g., as would be the case if the texturing was applied to the cover layer substrate. The texturing may be applied uniformly over the entire bonding surface of interest. Alternatively, the texturing may be applied only in those areas where sealing is desired, e.g. immediately surrounding the channels and chambers of the device.

Because the channel structures that are defined within the devices of the present invention have depths that typically range from about 5 µm to about 100 µm, it is generally desirable to provide surface texturing having substantially less depth. In preferred aspects, the texturing is provided having a height (or depth) that is from about 1% to about 50% of the channel depth, and preferably, from about 1% to about 30% of the channel depth, and still more preferably, between about 1% and about 10% of the channel depth. Accordingly, while the texturing may vary depending upon the depth of the channels of the device, the surface texturing as described herein will typically range from about 0.1 µm to about 50 µm high (or deep), and preferably, from about 0.25 µm to about 30 µm, and more preferably, from about 0.25 µm to about 10 µm high (or deep). For channels that are on the order of 10 to 20 µm deep, surface texturing of between about 0.5 to about 2 µm in depth is generally preferred.

In thermal bonding methods, the surface texturing serves to provide localized areas at which melting and bonding occur between substrate layers, preventing such occurrences within the channel structures per se, and thus preventing substantial channel distortion. In particular, because pressure between two substrates is concentrated in the raised texture structures it requires a lower overall substrate temperature to produce the desired bonding between the substrates, e.g., the combined pressure and temperature effects are concentrated at the raised ridges/structures. Further, as the texture structures are melted and flattened during the bonding process, the amount of surface area in contact between the two substrates increases, thereby reducing the localized pressure/heating effects. This increase in surface area and effective decrease in the localized pressure creates a bonding process that is somewhat self-regulating. In particular, after the surface texturing is distorted or flattened enough by the heat and pressure, the contact area between the substrates increases, thereby effectively reducing the localized pressure, which results in a considerable slowing of deformation. Specifically, the constant force applied to the texture structures is dissipated over a larger substrate surface as these textures collapse into the rest of the substrate surface, thereby arresting the melting and bonding process.

Figure 4:
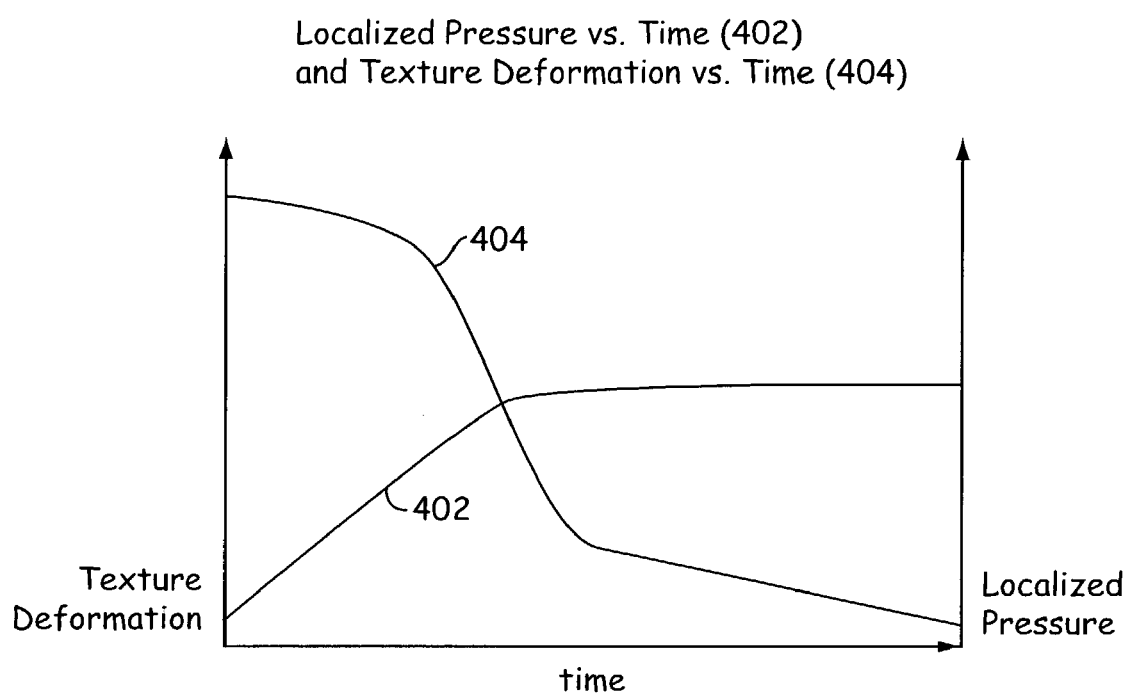
FIG. 4 illustrates a plot of both structural deformation of surface textures in the mating of two substrates as well as local pressure on the raised portions of the textures over time of the thermal bonding process.

This self-regulating process is illustrated in FIG. 4, which is a superimposed graph of localized pressure versus time 402 and texture deformation versus time 404. In particular, the local pressure at the interface of two substrates, e.g., at the top of the texturing (ridges, posts, etc.) at the beginning of the thermal bonding process, is spread over only the area of the interface. As the texturing (ridges, posts, etc.) melts during the thermal process, the area of the interface increases as the texturing flattens out. Accordingly, the same amount of applied force is spread over a wider area, until the texturing is nearly completely flattened out, at which point the pressure at the interfacing surfaces stabilizes at nor near the total applied pressure (as the interface is substantially a single surface, thus local pressure=total pressure).

Figure 3A:
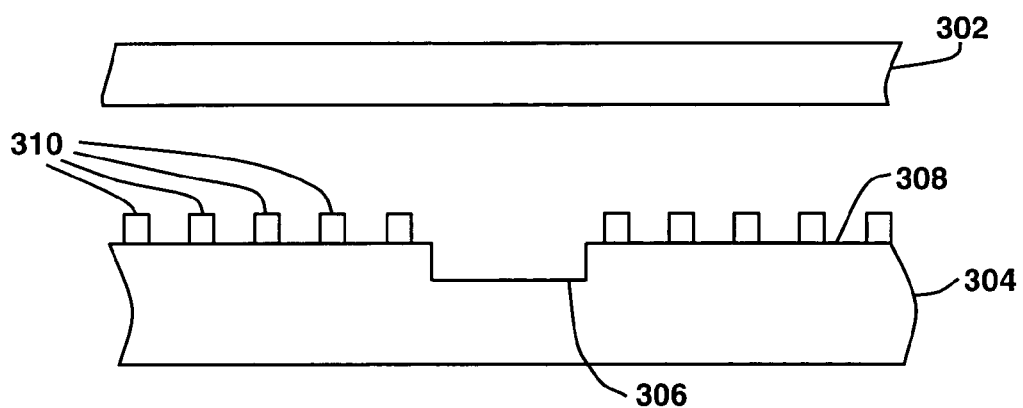
FIGS. 3A and 3B illustrate the bonding layer both before and after the bonding process, respectively.
Figure 3B:
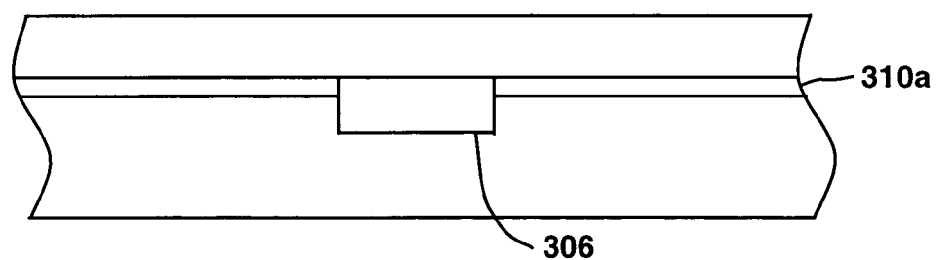

FIG. 3A illustrates the use of surface texturing in the bonding methods described herein. As shown, the upper substrate/cover layer 302 is mated with the lower substrate 304 that includes a channel 306 fabricated into its surface. The upper surface 308 of the bottom substrate 304 has provided thereon a surface texturing that includes a plurality of raised ridges 310, or raised posts/pillars on the bonding surface of the channel bearing substrate. The upper substrate 302 is mated to the lower substrate under appropriate pressure and temperature conditions. In preferred aspects, the applied temperature is typically at or above the transition temperature for the lower substrate, but well below the transition temperature of the upper substrate. Under the elevated temperature conditions, the focused pressure upon the texturing structures 310 melts and spreads the texture structures and bonds with the upper substrate 302. This is illustrated in FIG. 3B, where the collapsed or melted texture structures 310a form the bond point between the two substrate layers 302 and 304. Although preferred aspects utilize two substrates having different transition temperatures, this is not necessarily required. In particular, because the microstructures permit the focusing of pressure on those texturing structures, lower pressures may be used in the thermal bonding process. As noted previously, excessive applied pressures are at least partially to blame for the channel deformations described above. Therefore, by reducing the applied pressures, one also reduces the severity of channel deformation.

Although the surface textured methods described herein are generally in reference to thermal bonding methods, such techniques are also applicable to acoustic or sonic welding or bonding techniques. In particular, the raised elements of the surface texturing described herein, generally function in a manner similar to energy directors in conventional acoustic welding techniques. In use, the substrate layers are mated together and an appropriate pressure is applied. One or both of the substrates is then acoustically vibrated, e.g., at greater than about 10 to 20 KHz. The vibrational friction caused at the contact point between the two surfaces, e.g., on the texture elements or ridges, results in a localized heating, melting and bonding of the substrate layers. Further, as with the thermal bonding methods, once the texture elements have completely melted or compressed into their respective surfaces, the applied pressure is spread over the entire surface area, and melting and bonding cease. Again, this prevents substantial distortion of the channels. Acoustic welding methods and systems have been described in the art, and are commercially available, e.g., from Hermann Ultrasonics, Inc.

IV. Other Polymer Selection Criteria

In addition to selecting polymeric substrates based upon their transition temperatures, there are also a number of other criteria one can apply in polymer selection. For example, the microfluidic devices of the present invention are often used in the performance of analytical operations which employ optical detection systems. Such devices typically include a detection window disposed across one of the channels of the device and through which an optical signal can pass. As such, polymeric materials that are transparent are generally used in the fabrication of such devices. In particularly preferred aspects, fluorescent detection systems are utilized. This generally dictates that polymer grades be selected that have minimal levels of background or autofluorescence. Typically, auto-fluorescence is lower in certain polymer types, e.g., polymethylmethacrylate, as well as in more pure grades of polymers. Table 2 illustrates a comparison of the autofluorescence of different types and grades of polymers as compared to different types of glass.

Selection of an appropriate polymer type and grade generally depends upon the type of detection system utilized, the wavelength of light applied to the system, and the like. In general, however, the background fluorescence of the polymer substrate is less than 5 times that of glass, preferably less than twice that of glass, and more preferably, approximately the same as or less than glass, for the desired wavelength.

In addition to detection criteria, polymer substrates are also optionally selected for their ability to support or eliminate electroosmotic flow. In particular, as described in U.S. Ser. No. 08/843,212 filed Apr. 14, 1997 (incorporated herein by reference for all purposes), polymeric substrates may be selected or treated to support a desired level of electroosmotic flow, depending upon the application to which the device is going to be put. In particular, some polymeric materials have a sufficiently high level of surface charge to allow adequate electroosmotic flow in microscale channels fabricated from those materials. Electroosmotic flow is generally a desirable characteristic where the device is utilized in applications that employ bulk fluid flow within the channel networks, whereas certain other applications, e.g., nucleic acid separations, generally seek to eliminate such flow. Again, polymers may be selected to achieve this latter goal.

The present invention is illustrated in greater detail with reference to the following nonlimiting examples.

EXAMPLES

Example 1

Polymer Selection

Polymers were selected based upon their clarity, low fluorescence, processability and commercial availability. Several polymer materials were evaluated, as set forth in Table 1, below.

TABLE 1

| Property | Acrylite M-30 (Acrylic) | Acrylite L-40 (Acrylic) | Plexiglas VS UVT (Acrylic) | Makrolon DP-1-1265 (Polycarb.) | Lexan OQ1020L (Polycarb.) |
|---|---|---|---|---|---|
| Transmittance | 92 | 92 | 92 | 89 | 90 |
| Haze (%) | <1 | 2 | 2 | . . . | . . . |
| Melt Flow Rate (g/10 min) | 24 (all at 230° C., 3.8 kg) | 28 | 24 | 75 | 65 |
| Refract. Index | 1.49 | 1.49 | 1.49 | 1.582 | 1.58 |
| Dielectric Strength (kV/mm) | 19.7 | 19.7 | . . . | >16 | 14.8–17.6 |
| Vol. Resistivity (Ohm/cm) | . . . | . . . | . . . | $1.0 \times 10^{16}$ | $1.0 \times 10^{17}$ |
| Supplier | CYRO Indust. | Cyro Indust. | Atohaas, North Am. | Bayer | GE Plastics |

Based upon the results shown in Table 1, acrylic polymers, and particularly polymethylmethacrylate were selected as the best polymer substrate, with polycarbonate being the next best selection. Further tests were performed on these polymers and the results are shown in Table 2. Polymer resins were tested using injection molded test plates.

Fluorescence was measured using the following conditions:

| Excitation Wavelengths | 450–480 nm |
|---|---|
| Emission Wavelengths | 510–549 nm |

TABLE 2

| | Material | Thickness | Fluorescent Counts | Softening Point/$T_g$ |
|---|---|---|---|---|
| PMMA | Acrylite M-30 | 1.0 mm | 1,720 | 90° C. |
| | Plexiglas UVT | 1.0 mm | 1,800 | 87° C./91° C. |
| | Acrylite L-40 | 1.0 mm | 1,100 | 82° C. |

TABLE 2-continued

| | Material | Thickness | Fluorescent Counts | Softening Point/$T_g$ |
|---|---|---|---|---|
| Polycarbonate | Makrolon DP1-1265 | 1.0 mm | 12,300 | 144° C. |
| | Lexan OQ 1020L | 1.0 mm | 14,800 | — |
| Glass | White Crown (Hoya) | 2.8 mm | 500 | |
| | White Crown (Schott) | 3.0 mm | 400 | |
| | Green Soda Lime | 2.3 mm | 1,080 | |

Example 2

Thermal Bonding of Polymer Substrates

Figure 5A:
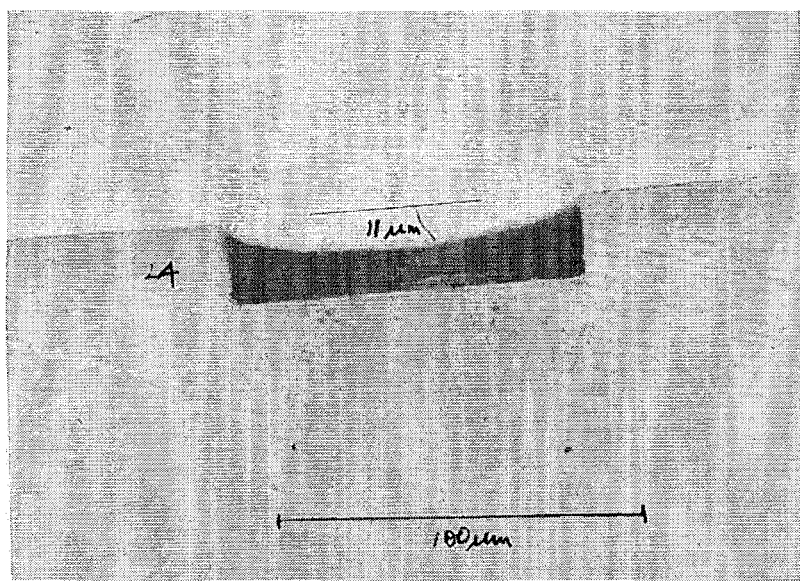
FIG. 5A illustrates a channel in which an upper substrate is protruding into the channel, whereas the channel shown in FIG. 5B is substantially clear of obstruction from the upper substrate.
Figure 5A:
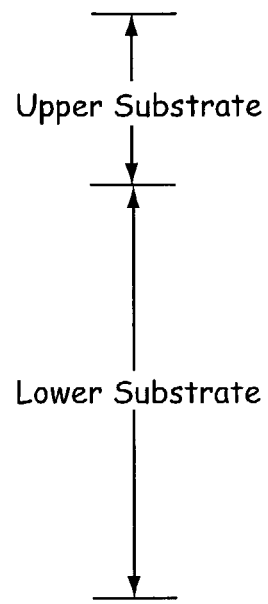
Figure 5B:
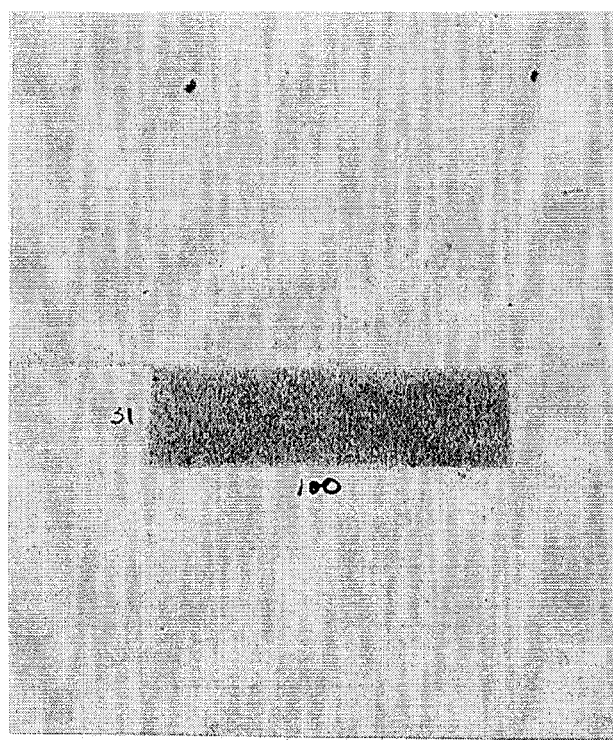
FIG. 5 is a cross-section of two channels thermally bonded together.
Figure 5B:
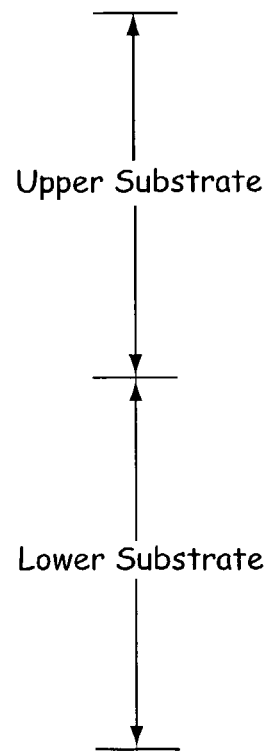

Initial bonding experiments utilized an embossed channel plate (substrate) fabricated from Plexiglas clear 99530 (described above). The channels had dimensions of 100 μm wide and 32 μm deep. A L-40 PMMA cover plate was thermally bonded to the channel plate at 84° C., the softening point of the L-40 polymer, and with an applied force of approximately 10 kg. Cross-sectional examination of the bonded channel showed that while the embossed channel plate maintained its structure, the cover plate had deformed into the channel, as shown in FIG. 5A. The provided dimensions are approximate. The bonding temperature was then adjusted to 80° C., and the experiment repeated. In this latter experiment, the cross section of the bonded parts showed that the channel had achieved a good seal, the channel was not distorted, nor had the cover plate substantially flowed into the channel as shown in FIG. 5B.

All publications and patent applications are herein incorporated by reference to the same extent as if each individual publication or patent application was specifically and individually indicated to be incorporated by reference. Although the present invention has been described in some detail by way of illustration and example for purposes of clarity and understanding, it will be apparent that certain changes and modifications may be practiced within the scope of the appended claims.

What is claimed is:

1. A method of fabricating a microfluidic device, comprising:
providing a first substrate having at least a first surface and a second substrate having at least a first surface, wherein at least one of the first surface of the first substrate or the first surface of the second substrate comprises a textured surface having a plurality of texturing structures fabricated thereon, the textured surface not comprising an applied adhesive, and wherein at least one of the first surface of the first substrate or the first surface of the second substrate comprises a groove fabricated therein, the groove not forming a portion of the texturing structures; and
mating and bonding the first surface of the first substrate to the first surface of the second substrate, while at the same time deforming the textured surface, the groove defining a channel when the first and second substrates are mated and bonded.

2. The method of claim 1, wherein the texturing structures comprise a plurality of raised ridges.

3. The method of claim 1, wherein the texturing structures comprises a plurality of microscale posts.

4. The method of claim 1, wherein the step of mating and bonding comprises applying heat and pressure to the first and second substrates to thermally bond the first surface of the first substrate to the first surface of the second substrate.

5. The method of claim 1, wherein at least one of the first surface of the first substrate and the first surface of the second substrate comprises a plurality of grooves fabricated therein, the grooves defining an integrated channel network when the first and second substrates are mated and bonded, and wherein the texturing structures have a height that is no greater than 50% of a depth of the grooves.

6. The method of claim 1, wherein at least one of the first surface of the first substrate and the first surface of the second substrate comprises a plurality of grooves fabricated therein, the grooves defining an integrated channel network when the first and second substrates are mated and bonded, and wherein the texturing structures have a height that is between about 1% and about 50% of a depth of the grooves.

7. The method of claim 1, wherein at least one of the first surface of the first substrate and the first surface of the second substrate comprises a plurality of grooves fabricated therein, the grooves defining an integrated channel network when the first and second substrates are mated and bonded, and wherein the texturing structures have a height that is between about 1% and about 30% of a depth of the grooves.

8. The method of claim 1, wherein at least one of the first surface of the first substrate and the first surface of the second substrate comprises a plurality of grooves fabricated therein, the grooves defining an integrated channel network when the first and second substrates are mated and bonded, and wherein the texturing structures have a height that is between about 1% and about 10% of a depth of the grooves.

9. The method of claim 1, wherein at least one of the first surface of the first substrate and the first surface of the second substrate comprises a plurality of grooves fabricated therein, the grooves defining an integrated channel network when the first and second substrates are mated and bonded, and wherein the texturing structures have a height that is from about 0.25 μm to about 50 μm high.

10. The method of claim 1, wherein at least one of the first surface of the first substrate and the first surface of the second substrate comprises a plurality of grooves fabricated therein, the grooves defining an integrated channel network when the first and second substrates are mated and bonded, and wherein the texturing structures have a height that is from about 0.25 μm to about 30 μm high.

11. The method of claim 1, wherein at least one of the first surface of the first substrate and the first surface of the second substrate comprises a plurality of grooves fabricated therein, the grooves defining an integrated channel network when the first and second substrates are mated and bonded, and wherein the texturing structures have a height that is from about 0.25 μm to about 10 μm high.

12. The method of claim 1, wherein at least one of the first surface of the first substrate and the first surface of the second substrate comprises a plurality of grooves fabricated therein, the grooves defining an integrated channel network when the first and second substrates are mated and bonded, and wherein the texturing structures have a height that is from about 0.5 μm to about 2 μm high.

13. The method of claim 1, wherein the step of mating and bonding comprises ultrasonically welding the first surface of the first substrate to the first surface of the second substrate.

14. The method of claim 1, wherein the step of mating and bonding comprises thermally bonding the first surface of the first substrate to the first surface of the second substrate.

15. The method of claim 1, wherein the step of mating and bonding comprises sonically bonding the first surface of the first substrate to the first surface of the second substrate.

* * * * *